US012638430B2

(12) United States Patent (10) Patent No.: US 12,638,430 B2
Kubota et al. (45) Date of Patent: May 26, 2026

(54) ESTIMATION METHOD, PROGRAM, AND ESTIMATION SYSTEM

(71) Applicant: Panasonic Intellectual Property Management Co., Ltd., Osaka (JP)

(72) Inventors: Hirofumi Kubota, Osaka (JP); Shota Tsurui, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 18/849,135

(22) PCT Filed: Feb. 24, 2023

(86) PCT No.: PCT/JP2023/006667
§ 371 (c)(1),
(2) Date: Sep. 20, 2024

(87) PCT Pub. No.: WO2023/181778
PCT Pub. Date: Sep. 28, 2023

(65) Prior Publication Data
US 2025/0208105 A1 Jun. 26, 2025

(30) Foreign Application Priority Data
Mar. 24, 2022 (JP) ................................. 2022-048820

(51) Int. Cl.
*G01N 33/00* (2006.01)
(52) U.S. Cl.
CPC ....... *G01N 33/004* (2013.01); *G01N 33/0062* (2013.01)
(58) Field of Classification Search
CPC ............. G01N 33/004; G01N 33/0062; G01N 21/3504; G01N 33/0067; G06Q 10/04; F24F 2110/70; F24F 2120/10
(Continued)

(56) References Cited

U.S. PATENT DOCUMENTS

| | | |
|---|---|---|
| 2018/0088544 A1 | 3/2018 | Sawada et al. |
| 2021/0190360 A1 | 6/2021 | Lee |
| 2023/0107402 A1* | 4/2023 | Majer ..................... F24F 11/52 |
| | | 702/50 |

FOREIGN PATENT DOCUMENTS

| | | | |
|---|---|---|---|
| JP | 2003-344277 A | | 12/2003 |
| JP | 2007101435 A | * | 4/2007 |

(Continued)

OTHER PUBLICATIONS

International Search Report dated Apr. 25, 2023 issued in International Patent Application No. PCT/JP2023/006667, with English translation.

*Primary Examiner* — Eric Blount
(74) *Attorney, Agent, or Firm* — Rimon P.C.

(57) ABSTRACT

An estimation method includes an analysis step, an extraction step, an approximation step, a location information acquisition step, an estimation step, and a notification control step. The analysis step includes deriving, as analytic information, a carbon dioxide concentration distribution in a virtual space. The extraction step includes extracting, from the analytic information, information about a virtual carbon dioxide concentration distribution in a height direction. The approximation step includes establishing an analysis formula for approximating the carbon dioxide concentration distribution in the height direction. The location information acquisition step includes acquiring location information about a person. The estimation step includes estimating an actual carbon dioxide concentration distribution in a real space using the analysis formula and the location information. The notification control step includes making notification of information about the actual concentration distribution estimated in the estimation step.

9 Claims, 9 Drawing Sheets

(58) Field of Classification Search
USPC ............................................ 340/632; 702/50
See application file for complete search history.

(56)                    References Cited

FOREIGN PATENT DOCUMENTS

| JP | 2009156801 A | * | 7/2009 | ......... B60H 1/00978 |
| JP | 2018-048749 A | | 3/2018 | |
| WO | 2016/185630 A1 | | 11/2016 | |
| WO | WO-2021235139 A1 | * | 11/2021 | .............. F24F 11/63 |

* cited by examiner

ESTIMATION METHOD, PROGRAM, AND ESTIMATION SYSTEM

CROSS-REFERENCE OF RELATED APPLICATIONS

This application is the U.S. National Phase under 35 U.S.C. § 371 of International Patent Application No. PCT/JP2023/006667, filed on Feb. 24, 2023, which in turn claims the benefit of Japanese Patent Application No. 2022-048820, filed on Mar. 24, 2022, the entire disclosures of which Applications are incorporated by reference herein.

TECHNICAL FIELD

The present disclosure generally relates to an estimation method, a program, and an estimation system, and more particularly relates to an estimation method, a program, and an estimation system, all of which may be used to estimate a carbon dioxide concentration in an indoor space.

BACKGROUND ART

Patent Literature 1 discloses a wide area distribution monitoring device for calculating a carbon dioxide concentration in a given space by making measurement of the space using a path configuration optical system and using a weight distribution function.

CITATION LIST

Patent Literature

Patent Literature 1: JP 2003-344277 A

SUMMARY OF INVENTION

If there is any person in a space (indoor space), his or her exhaled breath contains carbon dioxide, which affects the concentration of carbon dioxide in the indoor space.

In view of the foregoing background, it is therefore an object of the present disclosure to provide an estimation method, a program, and an estimation system, all of which may be used to estimate a carbon dioxide concentration distribution in an indoor space in a situation where any person is present in the indoor space.

An estimation method according to an aspect of the present disclosure includes an analysis step, an extraction step, an approximation step, a location information acquisition step, an estimation step, and a notification control step. The analysis step includes doing simulations to derive, as analytic information, a carbon dioxide concentration distribution in a virtual space. The simulations are done based on three-dimensional information about an indoor space, first environmental information about an environment in the indoor space, second environmental information about an outdoor environment, and virtual location information about a person's location that has been set in the virtual space corresponding to the indoor space. The extraction step includes extracting, from the analytic information, information about a virtual carbon dioxide concentration distribution at a point which has been arbitrarily set in a height direction in the virtual space. The approximation step includes establishing an analysis formula for approximating the carbon dioxide concentration distribution in the height direction based on the information about the virtual carbon dioxide concentration distribution extracted in the extraction step.

The location information acquisition step includes acquiring location information about the person who is present in a real space within the indoor space. The estimation step includes estimating an actual carbon dioxide concentration distribution in the real space using the analysis formula established in the approximation step and the location information acquired in the location information acquisition step. The notification control step includes making notification of information about the actual carbon dioxide concentration distribution estimated in the estimation step.

A program according to another aspect of the present disclosure is designed to cause one or more processors to perform the estimation method described above.

An estimation system according to still another aspect of the present disclosure includes an analyzer, an extractor, an approximator, a location information acquirer, an estimator, and a notification controller. The analyzer does simulations to derive, as analytic information, a carbon dioxide concentration distribution in a virtual space. The simulations are done based on three-dimensional information about an indoor space, first environmental information about an environment in the indoor space, second environmental information about an outdoor environment, and virtual location information about a person's location that has been set in the virtual space corresponding to the indoor space. The extractor extracts, from the analytic information, information about a virtual carbon dioxide concentration distribution at a point which has been arbitrarily set in a height direction in the virtual space. The approximator establishes an analysis formula for approximating the carbon dioxide concentration distribution in the height direction based on the information about the virtual carbon dioxide concentration distribution extracted by the extractor. The location information acquirer acquires location information about the person who is present in a real space within the indoor space. The estimator estimates an actual carbon dioxide concentration distribution in the real space using the analysis formula established by the approximator and the location information acquired by the location information acquirer. The notification controller makes notification of information about the actual carbon dioxide concentration distribution estimated by the estimator.

DESCRIPTION OF EMBODIMENTS

A preferred embodiment of the present disclosure will now be described in detail with reference to the accompanying drawings. In the following description of embodiments, constituent elements illustrated on multiple drawings and having the same feature will be designated by the same reference sign and description thereof will be omitted herein to avoid redundancy. Note that the embodiment to be described below is only an exemplary one of various embodiments of the present disclosure and should not be construed as limiting. Rather, the exemplary embodiment may be readily modified in various manners depending on a design choice or any other factor without departing from the scope of the present disclosure. The drawings to be referred to in the following description of embodiments are all schematic representations. Thus, the ratio of the dimensions (including thicknesses) of respective constituent elements illustrated on the drawings does not always reflect their actual dimensional ratio.

As used herein, if something is "perpendicular to" something else, then these two things may naturally cross each other exactly at right angles but may also be generally perpendicular to each other within a certain tolerance range. That is to say, the angle formed between the two things that are perpendicular to each other falls within the range defined as a sum of 90 degrees plus the certain tolerance (of 10 degrees or less, for example). Likewise, as used herein, if something is "parallel to" something else, this phrase refers to a situation where the two things are exactly parallel to each other without crossing each other at all but also a situation where the two things are generally parallel to each other within a certain tolerance range. For example, as used herein, if something is "parallel to" something else, the tilt angle defined by one things with respect to the other may be equal to or less than 10 degrees.

(1) Overview

Figure 1:
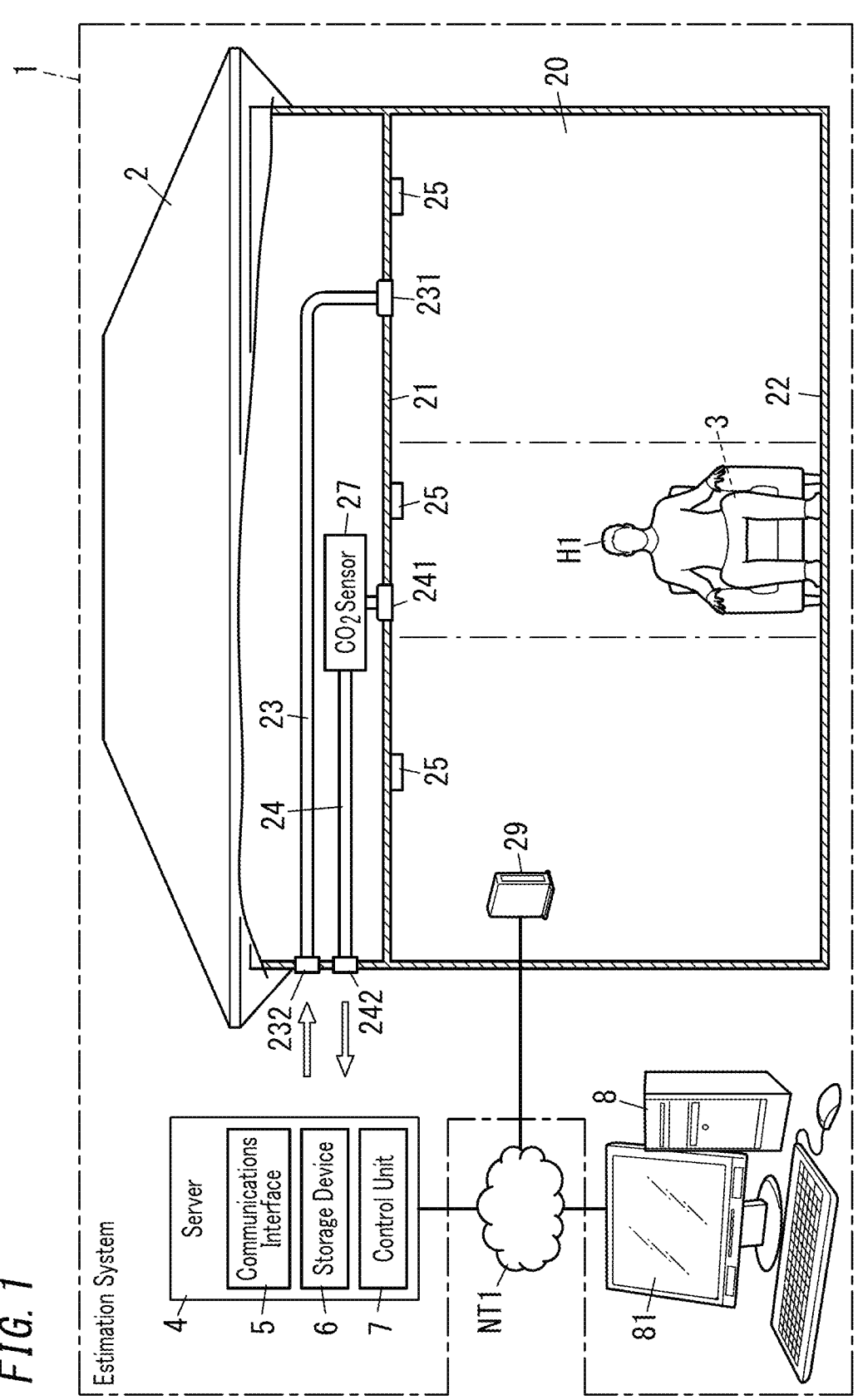
FIG. 1 is a schematic representation illustrating a configuration for an estimation system according to an exemplary embodiment.

First of all, an overview of an estimation system 1 and estimation method according to an exemplary embodiment will be described with reference to FIGS. 1-3. The estimation system 1 is a system that performs the estimation method. In this embodiment, a server 4 included in the estimation system 1 performs the estimation method.

This estimation method is designed to estimate a carbon dioxide (CO$_2$) concentration distribution in an indoor space 20 of a facility 2 where a person H1 is present. The person H1 may be, for example, a resident of the facility 2.

As used herein, examples of the "facility" include dwelling facilities for use for dwelling purposes and non-dwelling facilities such as stores (tenants' stores), offices, welfare facilities, educational institutions, hospitals, and factories. Examples of the non-dwelling facilities further include restaurants, amusement centers, hotels, inns, kindergartens, daycare facilities, and community centers. That is to say, the facility 2 may be a dwelling facility such as a multi-family dwelling house (i.e., a so-called "mansion" in Japan) or a non-dwelling facility such as an office building, whichever is appropriate. Alternatively, the facility 2 may also be a combination of a dwelling facility and a non-dwelling facility. For example, the facility 2 may include stores on lower floors thereof and dwelling units on upper floors thereof. In this embodiment, the facility 2 is supposed to be a single-family dwelling house.

In the indoor space 20, a plurality of (e.g., three in the example illustrated in FIG. 1) beacon terminals 25 are provided. The plurality of beacon terminals 25 are included in a local positioning system (LPS) for detecting the location of the person H1. The local positioning system according to this embodiment is a system for estimating, based on information about communications between the plurality of beacon terminals 25 and a mobile device 3 owned by a person H1, the location of the person H1 who carries the mobile device 3 with him or her.

Note that the phrase "carried by a person H1" as used herein refers to a situation where the person H1 carries the mobile device 3 which is put in his or her bag or a pocket of his or her clothes, a situation where the person H1 carries the mobile device 3 which is hooked on a strap, for example, and a situation where the person H1 holds the mobile device 3 on his or her hand. In the example illustrated in FIG. 1, the mobile device 3 is put in a pocket of the clothes that the person H1 wears.

The local positioning system according to this embodiment includes the mobile device 3. The mobile device 3 transmits location information, including information about communications between the mobile device 3 and the plurality of beacon terminals 25, to the server 4 via a communications module 29 and a network NT1.

Figure 2:
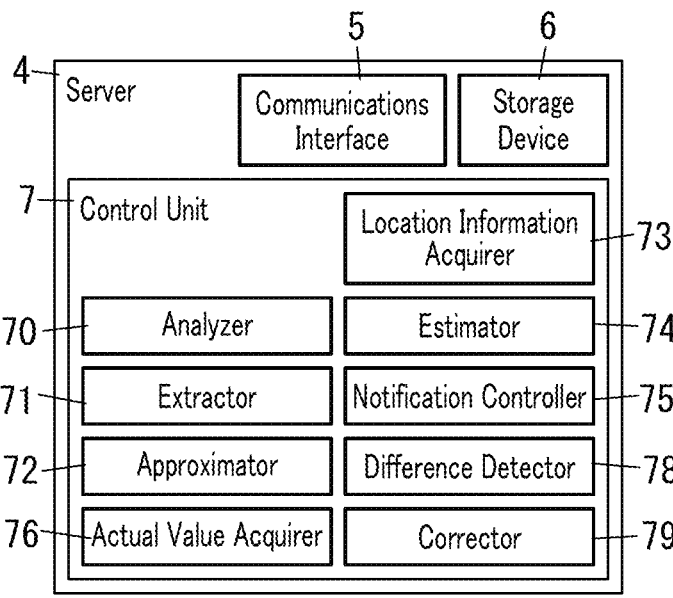
FIG. 2 is a block diagram illustrating a configuration for a server according to the exemplary embodiment.

As shown in FIG. 2, the server 4 according to this embodiment includes an analyzer 70, an extractor 71, an approximator 72, a location information acquirer 73, an estimator 74, and a notification controller 75.

The analyzer 70 performs analysis processing (analysis step). The analysis step includes doing simulations to derive, as analytic information, a carbon dioxide concentration distribution in a virtual space 20a (refer to FIG. 3) corresponding to the indoor space 20. The simulations are done based on three-dimensional information about the indoor space 20, first environmental information about an environment in the indoor space 20, second environmental information about an outdoor environment, and virtual location information about a person's H1a (refer to FIG. 3) location that has been set in the virtual space 20a corresponding to the indoor space 20.

The extractor 71 performs extraction processing (extraction step). The extraction step includes extracting, from the analytic information, information about a virtual carbon dioxide concentration distribution at a point which has been arbitrarily set in a height direction in the virtual space 20a. Note that the "height direction" as used herein is a direction parallel to the gravity direction.

The approximator 72 performs approximation processing (approximation step). The approximation step includes establishing an analysis formula for approximating the carbon dioxide concentration distribution in the height direction based on the information about the virtual carbon dioxide concentration distribution extracted in the extraction step.

The location information acquirer 73 performs location information acquisition processing (location information acquisition step). The location information acquisition step includes acquiring location information about the person (H1) who is present in a real space within the indoor space 20. In this embodiment, the location information is acquired from the mobile device 3 carried by the person H1 who is present in the indoor space 20.

The estimator 74 performs estimation processing (estimation step). The estimation step includes estimating an actual carbon dioxide concentration distribution in the real space within the indoor space 20 using the analysis formula established in the approximation step and the location information acquired in the location information acquisition step.

The notification controller 75 performs notification control processing (notification control step). The notification control step includes making notification of information about the actual carbon dioxide concentration distribution estimated in the estimation step.

The breath exhaled by the person H1 contains carbon dioxide. Thus, the carbon dioxide concentration distribution in the indoor space 20 where the person H1 is present is affected by the person's H1 location. The estimation system 1 and estimation method according to this embodiment enables accurately estimating, by using the location information about the person H1 who is present in the indoor space 20 and the analysis formula established based on simulations, the carbon dioxide concentration distribution in the indoor space 20 when the person H1 is present in the indoor space 20.

(2) Details

Next, a detailed configuration for the estimation system 1 according to this embodiment will be described with reference to FIGS. 1-5. As shown in FIG. 1, the estimation system 1 according to this embodiment includes equipments provided for the facility 2, the mobile device 3 carried by the person H1 who is present in the indoor space 20, the server 4, and an information terminal 8.

(2.1) Configuration for Facility

First, the details of the facility 2 will be described with reference to FIG. 1. As shown in FIG. 1, the facility 2 includes the indoor space 20, a supply air duct 23, and an exhaust duct 24.

The supply air duct 23 is an air passage which connects the space outside the facility 2 (i.e., the outside air) to the indoor space 20 of the facility 2 and is a duct for taking in the outside air and supplying the outside air to the indoor space 20. The supply air duct 23 includes a first air inlet 231 arranged to face the indoor space 20 (i.e., on the ceiling surface 21 of the indoor space 20) and a second air inlet 232 provided outside the facility 2. The second air inlet 232 may be provided with, for example, a supply air fan.

The exhaust duct 24 is an air passage that connects the space outside the facility 2 (i.e., the outside air) to the indoor space 20 of the facility 2 and is a duct for exhausting the air inside the indoor space 20 to the outside of the facility 2. The exhaust duct 24 includes a first exhaust port 241 arranged to face the indoor space 20 (i.e., on the ceiling surface 21 of the indoor space 20) and a second air outlet 242 provided outside the facility 2. The second air outlet 242 may be provided with, for example, an exhaust fan.

In addition, the facility 2 is further provided with multiple equipments included in the estimation system 1. The multiple equipments include the plurality of beacon terminals 25, a carbon dioxide ($CO_2$) sensor 27, and the communications module 29.

The plurality of beacon terminals 25 may be provided, for example, on the ceiling surface 21 of the indoor space 20. In the following description, if there is no need to distinguish the plurality of beacon terminals 25 from each other, then each of the plurality of beacon terminals 25 will be hereinafter referred to as a "beacon terminal 25."

Each beacon terminal 25 is configured to be able to transmit a beacon signal to the mobile device 3 carried by the person H1 with him or her to generate location information in response to the beacon signal. That is to say, the beacon terminal 25 according to this embodiment serves as a beacon transmitter. The beacon terminal 25 transmits a beacon signal in compliance with a predetermined communications protocol. The predetermined communications protocol may be, for example, a communications protocol such as the Bluetooth® Low Energy (BLE) protocol. Note that the predetermined communications protocol does not have to be the BLE protocol but may also be a communications protocol such as Wi-Fi®. The beacon terminal 25 transmits the beacon signals at regular time intervals and with predetermined transmission power. The beacon signal includes pieces of unique information (identification information) unique to the plurality of beacon terminals 25.

The $CO_2$ sensor 27 is a sensor for detecting the concentration value of carbon dioxide contained in the air. The $CO_2$ sensor 27 is provided near the first exhaust port 241 of the exhaust duct 24. Nevertheless, the $CO_2$ sensor 27 only needs to be provided at any position where the $CO_2$ sensor 27 may detect the concentration of carbon dioxide in the indoor space 20, and therefore, does not have to be provided near the first exhaust port 241. The $CO_2$ sensor 27 is configured to be ready to communicate with the communications module 29. The $CO_2$ sensor 27 transmits information about the carbon dioxide concentration detected to the communications module 29.

As used herein, the phrase "to be ready to communicate" means being able to transmit and receive information either directly or indirectly via a network or a relay, for example, by an appropriate wired or wireless communication method.

The communications module 29 is connected to the network NT1 such as the Internet. The communications module 29 according to this embodiment may be, for example, a router. The communications module 29 transmits information about the carbon dioxide concentration, which has been detected by the $CO_2$ sensor 27, to the server 4 via the network NT1. In addition, the communications module 29 according to this embodiment also transmits the location information that the communications module 29 has received from the mobile device 3 to the server 4 via the network NT1. Optionally, the communications module 29 may also transmit, to the server 4, information about an operating status indicating whether the supply air fan and the exhaust fan are operating properly and information about an operating status of air conditioning equipment such as an air conditioner provided in the indoor space 20.

(2.2) Configuration for Mobile Device

The mobile device 3 may be, for example, a mobile device, such as a smartphone, a tablet computer, or a laptop personal computer, carried by the person H1 with him or her. In this embodiment, the mobile device 3 is a smartphone as an example.

The mobile device 3 is configured to be ready to communicate with the plurality of beacon terminals 25 and the communications module 29. The mobile device 3 receives the beacon signal transmitted by each of the beacon terminals 25. That is to say, the mobile device 3 according to this embodiment serves as a beacon receiver. In addition, the mobile device 3 also transmits location information, including information about the communications (hereinafter referred to as "communication information") with the plurality of beacon terminals 25, to the server 4 via the communications module 29, for example. The communication information includes the received signal strength indication (RSSI) of the beacon signal and the identification information of the beacon terminal 25 included in the beacon signal. Alternatively, the mobile device 3 may transmit the location information to the server 4 via the cellular phone network (carrier network) provided by a communications service provider, not via the communications module 29.

The location information may include the identification information of the mobile device 3. The identification information of the mobile device 3 is information including, for example, a media access control (MAC) address, an Internet protocol (IP) address, or a product serial number.

(2.3) Configuration for Information Terminal

The information terminal 8 may be, for example, a desktop personal computer or a laptop personal computer. The information terminal 8 may be, for example, a terminal to be operated by a resident of the facility 2 (such as the person H1) or an employee of a company that provides the service of monitoring (or managing) the facility 2. The information terminal 8 is configured to be ready to communicate with the server 4 via the network NT1.

The display device 81 may be, for example, a liquid crystal display or an organic electroluminescent (EL) display. The display device 81 presents an on-screen image D1 (refer to FIG. 4) on its monitor screen under the control of the notification controller 75 of the server 4.

(2.4) Configuration for Server

The server 4 is an information terminal installed, for example, at a company that provides the service of monitoring (or managing) the environment in the indoor space 20 of the facility 2

As shown in FIG. 2, the server 4 includes a communications module 5, a storage device 6, and a control unit 7.

The server 4 may include, for example, a microcomputer including a processor and a memory. The computer system performs the functions of the control unit 7 by making the processor execute one or more appropriate programs. That is to say, the control unit 7 is implemented as a computer system including the processor and the memory. Each of the one or more programs may be stored in advance in the memory. Alternatively, the program may also be downloaded via a telecommunications line such as the Internet or distributed after having been stored in a non-transitory storage medium such as a memory card.

The communications module 5 is configured to be ready to communicate with the communications module 29 provided for the facility 2, the mobile device 3 carried by the person H1 with him or her, and the information terminal 8.

The storage device 6 may be a semiconductor memory such as a read-only memory (ROM), a random-access memory (RAM), or an electrically erasable programmable read-only memory (EEPROM). Nevertheless, the storage device 6 does not have to be a semiconductor memory but may also be, for example, a hard disk drive. The storage device 6 according to this embodiment stores location information about each of the plurality of beacon terminals 25, the three-dimensional information about the indoor space 20, first environmental information about the environment in the indoor space 20, second environmental information about an outdoor environment, and virtual location information about the person's H1a (refer to FIG. 3) location which has been set in a virtual space 20a corresponding to the indoor space 20.

The three-dimensional information about the indoor space 20 may be, for example, three-dimensional modeling data such as building information modeling (BIM) data of the facility. The first environmental information includes air conditioning equipment information including pieces of information about the performance, installation location, driving condition, and other parameters of air conditioning equipment installed in the indoor space 20 and ventilation equipment information including pieces of information about the performance, installation location, driving condition, and other parameters of ventilation equipment. The second environmental information includes pieces of information about the outside air temperature, the humidity, the season, and the carbon dioxide concentration in the outside air. The virtual location information includes status information indicating the location of the person H1a present in the virtual space 20a and also indicating whether the person H1a is seated or standing and information about the number of persons H1a present in the virtual space 20a. The first environmental information, the second environmental information, and the virtual location information are pieces of information to be used by the analyzer 70 to do simulations and have been set in advance before the analyzer 70 does simulations.

The control unit 7 includes the analyzer 70, the extractor 71, the approximator 72, the location information acquirer 73, the estimator 74, the notification controller 75, an actual value acquirer 76, a difference detector 78, and a corrector 79.

As described above, the analyzer 70 performs the analysis processing (analysis step). The analyzer 70 performs the analysis step before the facility 2 is built or before the resident starts living in the facility 2, for example. The analysis step includes doing simulations by the finite element method, for example, thereby deriving, as analytic information, a carbon dioxide concentration distribution in the virtual space 20a (refer to FIG. 3) corresponding to the indoor space 20. The simulations are done based on the three-dimensional information about the indoor space 20, the first environmental information about the environment in the indoor space 20, the second environmental information about the outdoor environment, and the virtual location information about the person's H1 location that has been set in the virtual space 20a corresponding to the indoor space 20. The analysis step includes making the storage unit 6 store the analytic information thus derived. Note that the analysis step according to this embodiment includes doing simulations multiple times with the settings of the first environmental information, the second environmental information, or the virtual location information changed every time and accumulating the results of analysis (i.e., results of simulations) as the analytic information.

As described above, the extractor 71 performs the extraction processing (extraction step). The extraction step includes extracting, from the analytic information, information about a virtual carbon dioxide concentration distribution at a point which has been arbitrarily set in the height direction in the virtual space 20a.

Figure 3:
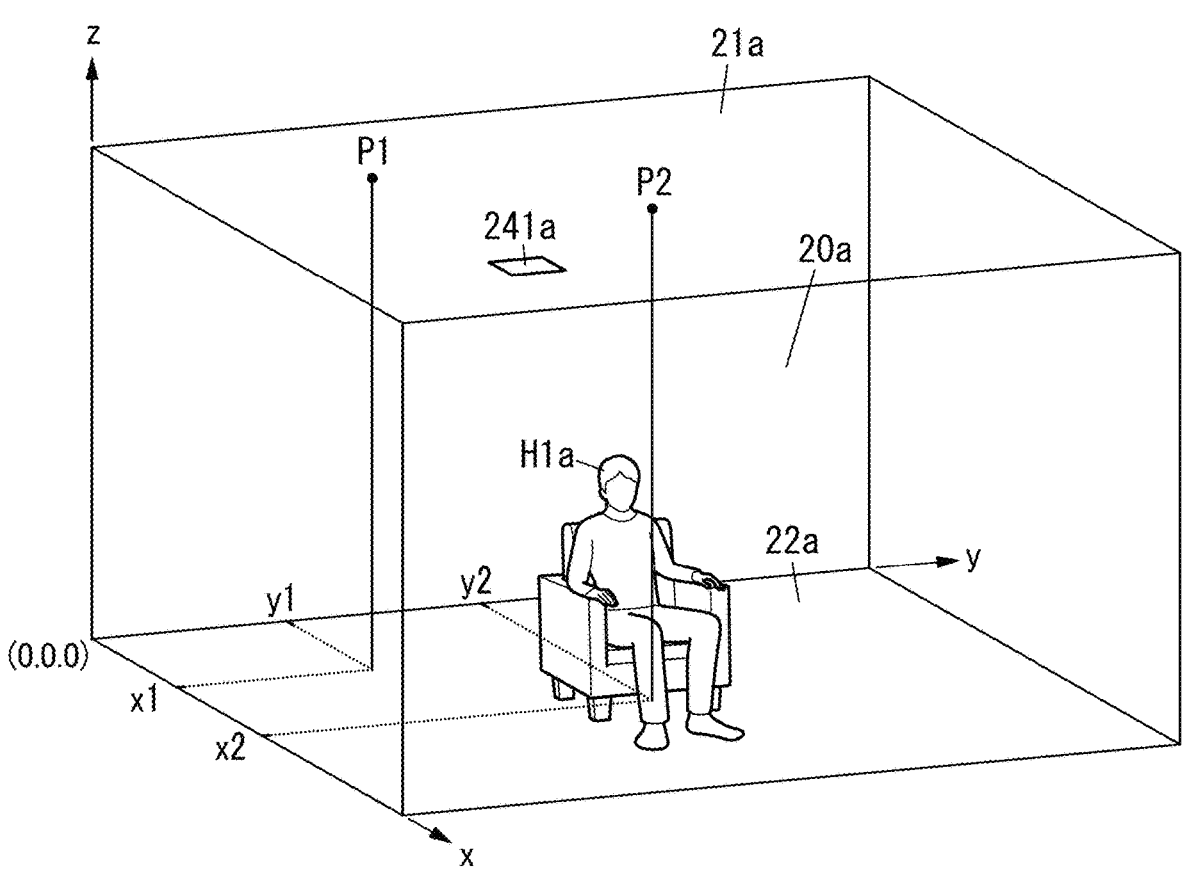
FIG. 3 is a schematic representation illustrating a virtual space corresponding to an indoor space according to the exemplary embodiment.

FIG. 3 is a schematic representation illustrating a virtual space 20a corresponding to the indoor space 20. In FIG. 3, the z-axis is an axis aligned with the height direction (i.e., the gravity direction) in the indoor space 20. The x-axis and the y-axis are axes perpendicular to not only the z-ax but also each other. The virtual space 20a has been created to have the same shape and the same dimensions as the indoor space 20. For example, the height as measured from a floor surface 22a of the virtual space 20a to a ceiling surface 21a thereof is the same as the height as measured from a floor surface 22 of the indoor space 20 to the ceiling surface 21 thereof. In addition, a virtual person H1a corresponding to the person H1 is placed in the virtual space 20a. The analytic information includes information about a carbon dioxide concentration distribution in the virtual space 20a.

The extraction step includes extracting, from the analytic information, information about a virtual carbon dioxide concentration distribution at, for example, a point P1 on the ceiling surface 21 in the height direction. As used herein, the virtual carbon dioxide concentration distribution at the point P1 in the height direction refers to the virtual carbon dioxide concentration distribution in a space extending from the point P1 on the ceiling surface 21a through the floor surface 22a right under the point P1. As shown in FIG. 3, the point P1 is an arbitrary position where no person H1a is present in the height direction. In addition, the extraction step further includes extracting, from the analytic information, information about a virtual carbon dioxide concentration distribution at, for example, a point P2 on the ceiling surface 21 in the height direction. As shown in FIG. 3, the point P2 is an arbitrary position where the person H1a is present in the height direction.

Note that the extraction step according to this embodiment includes arbitrarily setting points such as the points P1 and P2 in the virtual space 20a upon the request of the person H1 (or user) who is a resident of the facility 2. As used herein, the "request" of the person H1 indicates in what status (or condition) the person H1 wants to use (or is going to use) the indoor space 20. Examples of the person's H1 requests include the person's H1 request for a place (where he or she would like to be seated) in the indoor space 20, his or her request for the number of persons who use the indoor space 20, and a his or her request (schedule) for the number of times of ventilation required.

The approximator 72 performs the approximation processing (approximation step). The approximation step includes establishing an analysis formula for approximating the carbon dioxide concentration distribution in the height direction based on the information about the virtual carbon dioxide concentration distribution extracted in the extraction step.

More specifically, the virtual carbon dioxide temperature distribution in the virtual space 20a may be represented as a function F (x, y, z), where x is a value on the x-axis shown in FIG. 3, y is a value on the y-axis shown in FIG. 3, and z is a value on the z-axis shown in FIG. 3. In this case, a function Vxy (z) representing a virtual carbon dioxide concentration distribution at a position (x, y) in the height direction when the function F (x, y, z) is subjected to variable separation into H (x, y)·Vxy (z) is the analysis formula for approximating the (virtual) carbon dioxide concentration distribution in the height direction.

The carbon dioxide contained in the breath exhaled by the person H1 rises, after he or she has exhaled the breath, on an updraft produced around his or her body due to his or her body temperature to be accumulated around the ceiling surface 21. That is why in short to medium term, the carbon dioxide concentration around the ceiling surface 21 tends to be higher than the carbon dioxide concentration around the floor surface 22. In addition, the carbon dioxide accumulated around the ceiling surface 21 spreads horizontally along the ceiling surface 21. On the other hand, in a long term, carbon dioxide is heavier than the air, and therefore, tends to be accumulated around the floor surface 22. The facility 2 is provided with ventilation equipment for supplying air and making ventilation and air conditioning equipment such as an air conditioner so that the air in the indoor space 20 is always diffused around. Consequently, the carbon dioxide is accumulated around the ceiling surface 21 in short to medium term and then exhausted by ventilation into the outdoor space. That is to say, the carbon dioxide concentration distribution in the indoor space 20 tends to have a higher carbon dioxide concentration around the ceiling surface 21 rather than around the floor surface 22.

Since the carbon dioxide concentration distribution in the indoor space 20 tends to have a higher carbon dioxide concentration around the ceiling surface 21 rather than around the floor surface 22, the carbon dioxide concentration distribution in the height direction may be easily represented by an analysis formula, which is a characteristic feature of the carbon dioxide concentration distribution in the height direction. If the carbon dioxide concentration distribution in the height direction is represented by Vxy (2), the carbon dioxide concentration distribution in the three-dimensional space (i.e., the indoor space 20) may be separated into a two-dimensional distribution (i.e., on an xy plane) and a one-dimensional distribution (i.e., in the z direction). That is to say, the three-dimensional carbon dioxide concentration distribution may be represented in a simplified form.

As described above, the location information acquirer 73 performs the location information acquisition processing (location information acquisition step). The location information acquisition step includes acquiring location information about the person H1 who is present in a real space within the indoor space 20. The location information acquisition step according to this embodiment includes acquiring (i.e., receiving) the location information from the mobile device 3 carried by the person H1 with him or her.

The location information acquirer 73 according to this embodiment performs the location estimation processing (location estimation step). The location estimation step includes estimating the location of the mobile device 3 based on the location information acquired from the mobile device 3. The location estimation step includes estimating the location of the mobile device 3 by performing, for example, trilateration based on the received signal strength of the beacon signal, the identification information of the beacon terminal 25 included in the beacon signal, and the location information of the beacon terminal 25.

The actual value acquirer 76 performs actual value acquisition processing (actual value acquisition step). The actual value acquisition step includes acquiring an actual value of a carbon dioxide concentration at a predetermined point in the real space within the indoor space 20. The actual value acquisition step according to this embodiment includes acquiring the actual value of the carbon dioxide concentration at the first exhaust port 241 provided for the real space within the indoor space 20. The actual value acquisition step according to this embodiment includes acquiring information about the carbon dioxide concentration detected by the $CO_2$ sensor 27 provided around the first exhaust port 241 by receiving the information from the $CO_2$ sensor 27 via the communications module 29, for example.

The difference detector 78 performs difference detection processing (difference detection step). The difference detection step includes detecting the difference between the actual value of the carbon dioxide concentration acquired in the actual value acquisition step and an analytic value of the carbon dioxide concentration at a predetermined point in the virtual space 20a which corresponds to the predetermined point in the real space. The difference detection step according to this embodiment includes detecting the difference between the actual value of the carbon dioxide concentration acquired in the actual value acquisition step and an analytic value of the carbon dioxide concentration at a first exhaust port 241a (exhaust port) provided for the virtual space 20a which corresponds to the first exhaust port 241 (exhaust port) provided for the real space.

The difference detection step according to this embodiment includes acquiring the analytic value of the carbon dioxide concentration at the first exhaust port 241a (which is an exemplary predetermined point) in the virtual space 20a from the analytic information stored in the storage device 6.

The corrector 79 performs correction processing (correction step). The correction step includes correcting the analysis formula established in the approximation step based on the difference detected in the difference detection step between the actual value of the carbon dioxide concentration and the analytic value thereof. For example, if the actual value of the carbon dioxide concentration is higher than the analytic value thereof, the correction step includes correcting the analysis formula to increase the result of the analysis formula by the difference between the actual value and the analytic value. On the other hand, if the analytic value of the carbon dioxide concentration is higher than the actual value thereof, the correction step includes correcting the analysis formula to decrease the result of the analysis formula by the difference between the actual value and the analytic value.

In the estimation system 1 and estimation method according to this embodiment, the analysis formula is corrected based on the difference in carbon dioxide concentration at a predetermined point (e.g., the first exhaust port 241 in this embodiment) within the indoor space 20, thus enabling estimating the carbon dioxide concentration distribution more accurately using a small number (e.g., only one in this embodiment) of sensors.

As described above, the estimator 74 performs the estimation processing (estimation step). The estimation step includes estimating an actual carbon dioxide concentration distribution in the real space within the indoor space 20 using the analysis formula established in the approximation step and the location information acquired in the location information acquisition step. More specifically, the estimation step according to this embodiment includes estimating an actual carbon dioxide concentration distribution in the real space within the indoor space 20 using the analysis formula corrected in the correction step and the location information acquired in the location information acquisition step.

As described above, the notification controller 75 performs the notification control processing (notification control step). The notification control step includes making notification of information about the actual carbon dioxide concentration distribution estimated in the estimation step. The notification control step according to this embodiment includes making notification of information about the actual carbon dioxide concentration distribution estimated in the estimation step by presenting the information on the display device 81 of the information terminal 8.

Figure 4:
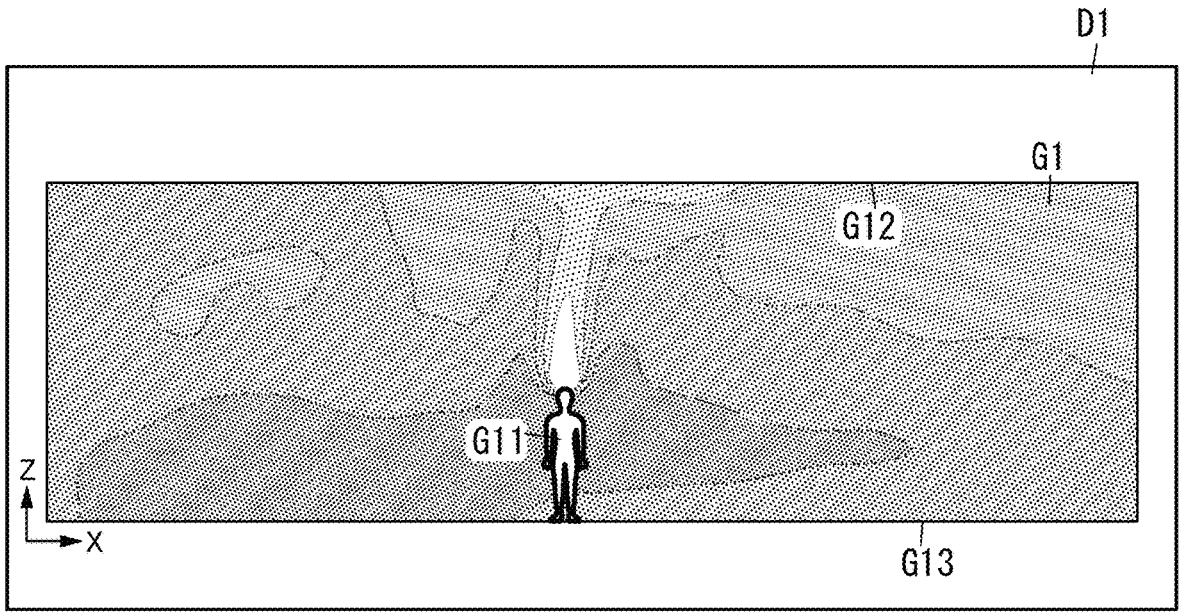
FIG. 4 is a schematic representation illustrating an on-screen image presented by the estimation system according to the exemplary embodiment.

As shown in FIG. 4, the notification control step according to this embodiment may include, for example, presenting, on the display device 81, an on-screen image D1 including an image G1 representing the actual carbon dioxide concentration distribution estimated in the estimation step. In the image G1, the higher the carbon dioxide concentration a given space has, the lighter (i.e., closer to the color white) the color in which the space is displayed is. On the other hand, the lower the carbon dioxide concentration a given space has, the darker (i.e., closer to the color black) the color in which the space is displayed is. In FIG. 4, the shades of the display colors are represented by dotted hatching in five levels, namely, from Level 1 through Level 5 (color white), for example. Note that the image G11 included in the image G1 represents the person H1, the image G12 represents the ceiling surface 21, and the image G13 represents the floor surface 22.

Alternatively, the notification control step may include making notification of information about the actual carbon dioxide concentration distribution (i.e., the on-screen image D1) by presenting the information on a display (such as the monitor screen of the mobile device 3) other than the display device 81.

In the estimation system 1 and estimation method according to this embodiment, information about the actual carbon dioxide concentration distribution estimated in the estimation step is presented on the display device 81 of the information terminal 8, thus allowing the user to visually recognize the information about the actual carbon dioxide concentration distribution.

(3) Operation of Estimation System

Next, it will be described with reference to FIG. 5 how the estimation system 1 operates.

First, the estimation system 1 performs analysis processing (analysis step) (in S1). Specifically, the estimation system 1 does simulations to derive, as analytic information, the carbon dioxide concentration distribution in the virtual space 20a corresponding to the indoor space 20.

Next, the estimation system 1 performs extraction processing (extraction step) (in S2). Specifically, the estimation system 1 extracts, from the analytic information, information about a virtual carbon dioxide concentration distribution at a point which has been arbitrarily set in the height direction in the virtual space 20a.

Subsequently, the estimation system 1 performs approximation processing (approximation step) (in S3). Specifically, the estimation system 1 establishes an analysis formula for approximating the carbon dioxide concentration distribution in the height direction based on the information about the virtual carbon dioxide concentration distribution extracted in the extraction step;

Thereafter, the estimation system 1 performs actual value acquisition processing (actual value acquisition step) (in S4). Specifically, the estimation system 1 acquires an actual value of the carbon dioxide concentration at a first exhaust port 241 (exhaust port) provided for the real space within the indoor space 20.

Then, the estimation system 1 performs difference detection processing (difference detection step) (in S5). Specifically, the estimation system 1 detects the difference between the actual value and analytic value of the carbon dioxide concentration.

Next, the estimation system 1 performs correction processing (correction step) (in S6). Specifically, the estimation system 1 according to this embodiment corrects the analysis formula based on the difference in carbon dioxide concentration detected in the difference detection step.

Subsequently, the estimation system 1 performs location information acquisition processing (location information acquisition step) (in S7). Specifically, the estimation system 1 acquires the location information about the person H1 who is present in the real space within the indoor space 20.

Thereafter, the estimation system 1 performs estimation processing (estimation step) (in S8). Specifically, the estimation system 1 according to this embodiment estimates an actual carbon dioxide concentration distribution in the indoor space 20 using the analysis formula corrected in the correction step and the location information acquired in the location information acquisition step.

Finally, the estimation system 1 performs notification control processing (notification control step) (in S9). Specifically, the estimation system 1 according to this embodiment makes notification by presenting, on the display device 81 of the information terminal 8, information about the actual carbon dioxide concentration distribution estimated in the estimation step.

Figure 5:
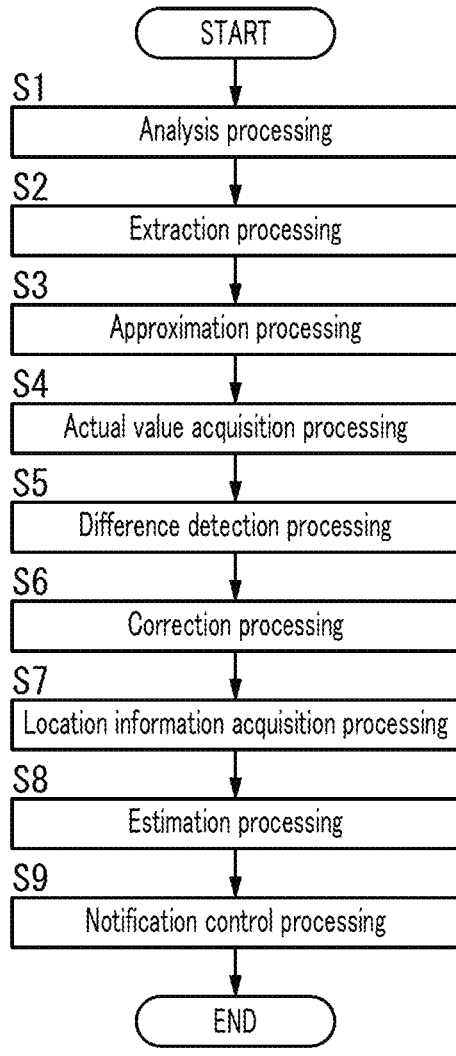
FIG. 5 is a flowchart showing how the server according to the exemplary embodiment operates.

Note that the flowchart shown in FIG. 5 shows just an exemplary procedure of the estimation method according to this embodiment. Thus, the processing steps shown in FIG. 5 may be performed in a different order as appropriate, an additional processing step may be performed as needed, or at least one of the processing steps shown there may be omitted as appropriate.

(4) Variations

Next, variations of the exemplary embodiment will be enumerated one after another. Note that the variations to be described below may be adopted in combination as appropriate.

(4.1) First Variation

The correction step may include correcting the analytic information based on the difference in carbon dioxide concentration detected in the difference detection step. In other words, the correction step may include correcting the results of the simulations obtained in the analysis step based on the difference in carbon dioxide concentration detected in the difference detection step.

It will be described with reference to FIG. 6 how the estimation system 1 according to the first variation may operate. First, the estimation system 1 performs the analysis processing (analysis step) (in S1).

Next, the estimation system 1 performs the actual value acquisition processing (actual value acquisition step) (in S4) and then performs the difference detection processing (difference detection step) (in S5).

Suppose, in this example, the actual value of the carbon dioxide concentration acquired in the actual value acquisition step is 550 ppm and the analytic value of the carbon dioxide concentration at a predetermined point (e.g., the first exhaust port 241*a*) in the virtual space 20*a* corresponding to the predetermined point (e.g., the first exhaust port 241) in the real space is 500 ppm. In that case, the difference in carbon dioxide concentration (i.e., the actual value minus the analytic value) calculated in the difference detection step is +50 ppm.

If the corrected result of simulations is SA (x, y, z), the result of simulations that has not been corrected yet is SB (x, y, z), and a correction term (i.e., the difference in carbon dioxide concentration) is y, then the corrected result of simulations may be given by the following Equation (1):

$$SA\,(x,\,y,\,z) = SB\,(x,\,y,\,z) + \gamma \tag{1}$$

The estimation system 1 performs the correction processing (correction step) (in S11). The correction step according to this first variation includes correcting, by this Equation (1), the result of simulations obtained in the analysis step.

Next, the estimation system 1 performs the extraction processing (extraction step) (in S12). The extraction step includes extracting information about the virtual carbon dioxide concentration distribution at a point which has been set arbitrarily in the height direction within the virtual space 20*a* (i.e., information about the corrected carbon dioxide concentration distribution) from the corrected analytic information including SA (x, y, z) representing the corrected result of simulations.

Next, the estimation system 1 performs the approximation processing (approximation step) (in S13). The approximation step includes establishing an analysis formula for approximating the carbon dioxide concentration distribution in the height direction based on the information about the virtual carbon dioxide concentration distribution (i.e., information about the corrected concentration distribution) extracted in the extraction step. The analysis formula established in the approximation step according to the first variation is based on the difference in carbon dioxide concentration detected in the difference detection step. As the analysis formula, a polynomial representing a linear function or a quadratic function, for example, may be used.

Then, the estimation system 1 performs the location information acquisition processing (location information acquisition step) (in S7), performs the estimation processing (estimation step) (in S8), and then performs the notification control processing (notification control step) (in S9).

In the estimation system 1 and estimation method according to this first variation, the analytic information is corrected based on the difference in carbon dioxide concentration at a predetermined point (e.g., the first exhaust port 241 in this first variation) within the indoor space 20, thus enabling estimating the carbon dioxide concentration distribution more accurately using a small number (e.g., only one in this first variation) of sensors.

Figure 6:
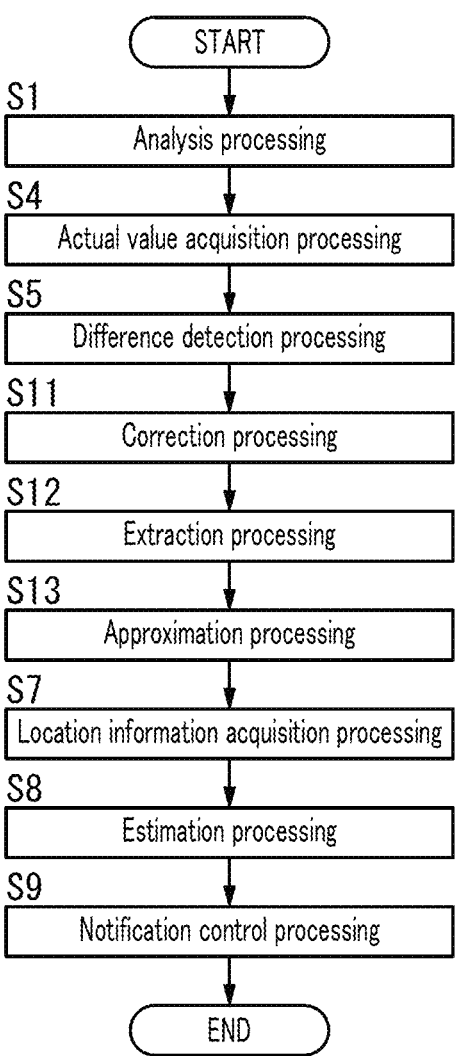
FIG. 6 is a flowchart showing how a server according to a first variation operates.

Note that the flowchart shown in FIG. 6 shows just an exemplary estimation method according to the first variation. Thus, the processing steps shown in FIG. 6 may be performed in a different order as appropriate, an additional processing step may be performed as needed, or at least one of the processing steps shown there may be omitted as appropriate.

(4.2) Second Variation

The estimation step may include estimating the actual carbon dioxide concentration distribution in the real space within the indoor space 20 with the horizontal direction (i.e., xy direction) of the function Vxy (z) spread. That is to say, the estimation step may include estimating the actual carbon dioxide concentration distribution in the real space within the indoor space 20 with the horizontal direction of the function Vxy (z) set within a predetermined range.

When the horizontal direction of the function Vxy (z) is set within the predetermined range, the carbon dioxide concentration distribution is supposed to be uniform in the horizontal direction. In the space A1 surrounding the person H1, the carbon dioxide concentration is locally higher than in any other space due to the breath exhaled by the person H1. However, the carbon dioxide diffuses mostly upward, and therefore, the amount of carbon dioxide that diffuses in the horizontal direction is relatively small. That is to say, even if the concentration of the carbon dioxide concentration in the horizontal direction in the space A1 surrounding the person H1 is approximated to be uniform, the carbon dioxide concentration distribution in the entire indoor space 20 is hardly affected, and therefore, the carbon dioxide concentration distribution in the horizontal direction is supposed to be uniform.

For example, the estimation step may include approximating the shape of the carbon dioxide concentration distribution in the space A1 surrounding the person H1 present in the indoor space 20 to be a predetermined stereoscopic shape. The carbon dioxide concentration distribution in the height direction inside the predetermined stereoscopic shape is based on the function Vxy (z) as the analysis formula. The carbon dioxide concentration distribution in the horizontal direction inside the predetermined stereoscopic shape is uniform.

Figure 7:
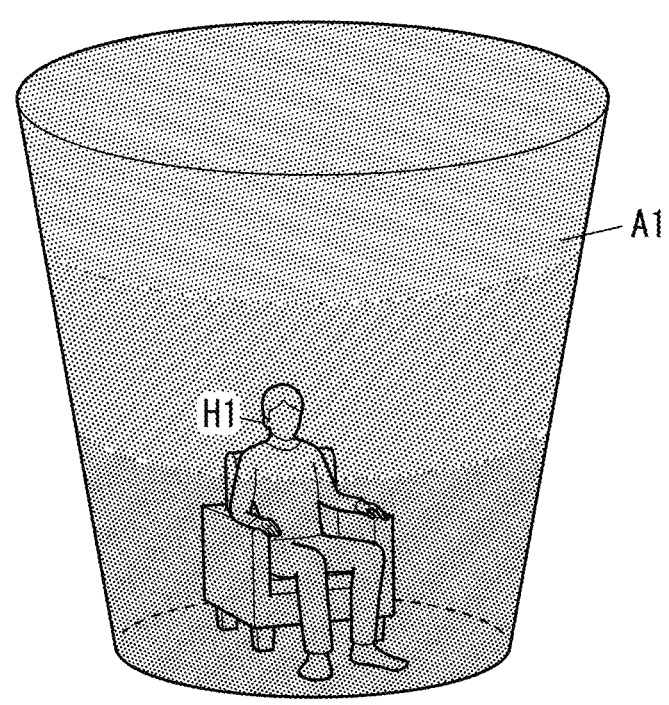
FIG. 7 is a schematic representation illustrating an exemplary approximated shape of a carbon dioxide concentration distribution in a space surrounding a person according to a second variation.

As shown in FIG. 7, the predetermined stereoscopic shape may be the shape of a truncated cone centered around the person H1. More specifically, the predetermined stereoscopic shape is the shape of a truncated cone, which is centered around the person H1, of which the upper and bottom surfaces are perpendicular to the height direction, and of which the horizontal cross-sectional area increases from the bottom surface toward the upper surface.

In the estimation system 1 and estimation method according to the second variation, the shape of the carbon dioxide concentration distribution in the space A1 surrounding the person H1 present in the indoor space 20 is approximated to be a predetermined stereoscopic shape, thereby simplifying the processing in the estimation step and shortening the time it takes to have the estimation step done. In addition, the predetermined stereoscopic shape according to this second variation is the shape of a truncated cone, of which the horizontal cross-sectional area increases from the bottom surface toward the upper surface. Thus, the predetermined stereoscopic shape according to this second variation approximates the distribution of carbon dioxide which is accumulated around the ceiling surface 21 and spreads in the horizontal direction along the ceiling surface 21.

(4.3) Third Variation

Figure 8:
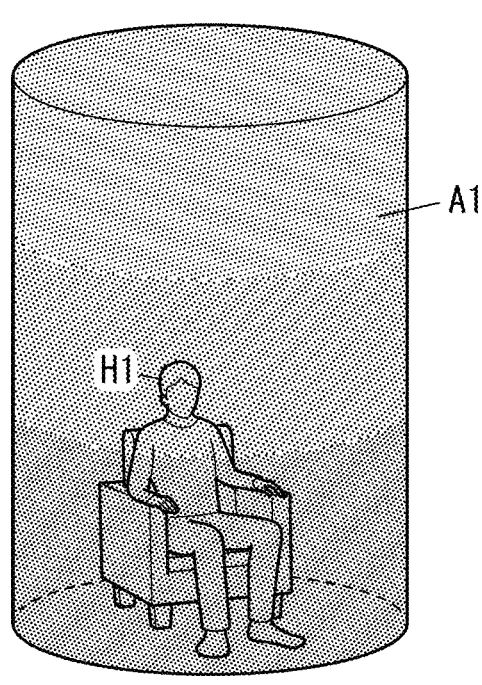
FIG. 8 is a schematic representation illustrating an exemplary approximated shape of a carbon dioxide concentration distribution in a space surrounding a person according to a third variation.

As shown in FIG. 8, the estimation step may include approximating the shape of the carbon dioxide concentration distribution in the space A1 surrounding the person H1 present in the indoor space 20 to be the shape of a circular column, of which the upper surface and bottom surface are perpendicular to the height direction. The predetermined stereoscopic shape according to the third variation is the shape of a circular column, of which the upper surface and bottom surface are perpendicular to the height direction, thus enabling further simplifying the processing in the estimation step and further shortening the time it takes to have the estimation step done.

Note that the predetermined stereoscopic shape according to the third variation is the shape of a circular column which is centered around the person H1 when viewed in plan in the height direction (i.e., in top view). In addition, the predetermined stereoscopic shape according to the third variation has a horizontal cross section with a radius of 0.5 m. The breath exhaled by the person H1 rises on an updraft produced around the person H1 within a range having a radius of approximately 0.5 m and centered around the person H1. The circular column, of which a horizontal cross section has a radius of 0.5 m, approximates the distribution of carbon dioxide rising on an updraft produced around the person H1.

Figure 9:
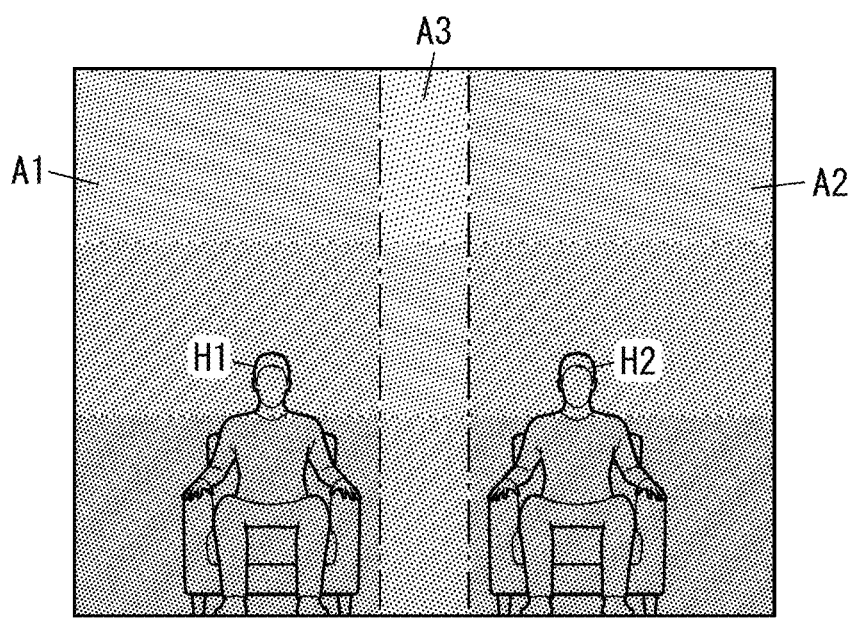
FIG. 9 is a schematic representation illustrating how to calculate a carbon dioxide concentration in a space surrounding persons according to the exemplary embodiment.

Also, as shown in FIG. 9, a person H1 (first person) and another person H2 (second person), different from the person H1, may be present in the indoor space 20. In the example shown in FIG. 9, the shape of the carbon dioxide concentration distribution in the space A1 surrounding the person H1 and the shape of the carbon dioxide concentration distribution in the space A2 surrounding the person H2 are both approximated to be the shape of a circular column, of which the upper surface and bottom surface are perpendicular to the height direction.

The estimation step includes estimating, if at least part of the space A1 (first space) and at least part of the space A2 (second space) overlap with each other, the carbon dioxide concentration distribution in a space A3 where the spaces A1 and A2 overlap with each other by adding the concentration of carbon dioxide in the space A2 to the concentration of carbon dioxide in the space A1. The space A1 is a space surrounding the person H1 who is present in the real space within the indoor space 20. The space A2 is a space surrounding the person H2 who is present in the real space within the indoor space 20.

Estimating, when the space A1 and the space A2 overlap with each other, the carbon dioxide concentration distribution in the space A3 by adding the concentration of carbon dioxide in the space A2 to the concentration of carbon dioxide in the space A1 allows the carbon dioxide concentration distribution in the indoor space 20 to be estimated more accurately.

Optionally, the predetermined stereoscopic shape may be the shape of a circular column, of which a horizontal cross section has a radius of 1.0 m. For example, if the person H1 is speaking (e.g., having a conversation with another person), the breath exhaled by the person H1 reaches a point more distant from the person H1 than in a situation where the person H1 is silent. That is why if a sound sensor or a camera, for example, detects that the person H1 is speaking, then the carbon dioxide concentration distribution in the space surrounding the person H1 may have the shape of a circular column, of which a horizontal cross section has a radius of 1.0 m. The circular column, of which a horizontal cross section has a radius of 1.0 m, approximates the shape of the carbon dioxide concentration distribution in a situation where the person H1 is speaking.

Optionally, the predetermined stereoscopic shape may also be, for example, the shape of a partially bulging circular column (i.e., in the shape of a barrel), which bulges locally in its part around the person's H1 face. The breath is exhaled by the person H1 from mostly the nose and mouth of his or her face into the indoor space 20 to spread in the horizontal direction (i.e., in the xy direction). Thus, the barrel shape approximates the actual carbon dioxide concentration distribution. The bulging part of the barrel may have a horizontal cross section with a radius of 1.0 m, for example.

(4.4) Other Variations

The functions of either the estimation system 1 (server 4) or estimation method according to the exemplary embodiment described above may also be implemented as, for example, a (computer) program or a non-transitory storage medium on which the program is stored. A program according to one aspect is designed to cause one or more processors to perform the estimation method described above for the exemplary embodiment.

The estimation system 1 (server 4) according to the present disclosure or the agent that performs the estimation method according to the present disclosure includes a computer system. The computer system may include a processor and a memory as principal hardware components thereof. The computer system performs the functions of the estimation system 1 according to the present disclosure or serves as the agent that performs the estimation method according to the present disclosure by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be made up of a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits such as an IC or an LSI include integrated circuits called a "system LSI," a "very-large-scale integrated circuit (VLSI)," and an "ultra-large-scale integrated circuit (ULSI)." Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be aggregated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

In the embodiment described above, the plurality of functions of the estimation system 1 are integrated together in a single housing (i.e., the server 4). However, this is not an essential configuration for the estimation system 1 and should not be construed as limiting. Alternatively, those constituent elements of the estimation system 1 may also be distributed in multiple different housings. Still alternatively, at least some functions of the estimation system 1 (e.g., some functions of the server 4) may be implemented as, for example, a cloud computing system as well.

Optionally, the mobile device 3 may estimate its own location based on a beacon signal. Specifically, the mobile device 3 may estimate its own location by performing, for example, trilateration based on the received signal strength of the beacon signal, the identification information of the beacon terminal 25 included in the beacon signal, and the location information of the beacon terminal 25. Then, the mobile device 3 transmits the result of estimation as location information to the server 4.

In the exemplary embodiment described above, the beacon terminal 25 is a beacon transmitter and the mobile device 3 is a beacon receiver. However, this is only an example and should not be construed as limiting. Alternatively, the beacon terminal 25 may also be a beacon receiver and the mobile device 3 may also be a beacon transmitter. If the beacon terminal 25 is a beacon receiver, then the beacon terminal 25, for example, may transmit location information to the server 4 via the communications module 29, for example.

The actual value acquisition step may include, for example, acquiring information about multiple carbon dioxide concentrations detected by a plurality of $CO_2$ sensors 27 provided at multiple different points in the indoor space 20, for example. In that case, the difference detection step includes acquiring, from the analytic information, multiple analytic values of carbon dioxide concentrations at multiple points in the virtual space 20a corresponding one to one to the multiple points in the real space. Then, the difference detection step includes detecting the differences between the multiple actual values acquired in the actual value acquisition step and multiple analytic values corresponding to the multiple actual values, respectively. The correction step includes correcting, based on the multiple differences detected in the difference detection step, either the analysis formula established in the approximation step or the analytic information (i.e., the result of simulations obtained in the analysis step). The correction step may include correcting, based on the average of the multiple differences, either the analysis formula established in the approximation step or the analytic information. Alternatively, the correction step may include dividing the indoor space 20 into multiple sub-spaces according to the multiple points where the plurality of $CO_2$ sensors 27 are provided and correcting, based on the difference between the actual value detected by the $CO_2$ sensor 27 provided in each of the multiple sub-spaces divided and a corresponding analytic value, either the analysis formula established in the approximation step or the analytic information.

(Recapitulation)

As can be seen from the foregoing description, an estimation method according to a first aspect includes an analysis step, an extraction step, an approximation step, a location information acquisition step, an estimation step, and a notification control step. The analysis step includes doing simulations to derive, as analytic information, a carbon dioxide concentration distribution in a virtual space (20a). The simulations are done based on three-dimensional information about an indoor space (20), first environmental information about an environment in the indoor space (20), second environmental information about an outdoor environment, and virtual location information about a person's (H1) location that has been set in the virtual space (20a) corresponding to the indoor space (20). The extraction step includes extracting, from the analytic information, information about a virtual carbon dioxide concentration distribution at a point which has been arbitrarily set in a height direction in the virtual space (20a). The approximation step includes establishing an analysis formula for approximating the carbon dioxide concentration distribution in the height direction based on the information about the virtual carbon dioxide concentration distribution extracted in the extraction step. The location information acquisition step includes acquiring location information about the person (H1) who is present in a real space within the indoor space (20). The estimation step includes estimating an actual carbon dioxide concentration distribution in the real space using the analysis formula established in the approximation step and the location information acquired in the location information acquisition step. The notification control step includes making notification of information about the actual carbon dioxide concentration distribution estimated in the estimation step.

This aspect enables accurately estimating, by using location information about a person (H1) who is present in an indoor space (20) and an analysis formula established based on simulations, a carbon dioxide concentration distribution in the indoor space (20) when the person (H1) is present in the indoor space (20).

An estimation method according to a second aspect, which may be implemented in conjunction with the first aspect, further includes an actual value acquisition step, a difference detection step, and a correction step. The actual value acquisition step includes acquiring an actual value of carbon dioxide concentration at an exhaust port (first exhaust port 241) provided for the real space. The difference detection step includes detecting a difference between the actual value acquired in the actual value acquisition step and an analytic value of carbon dioxide concentration at an exhaust port (first exhaust port 241a) provided in the virtual space (20a) which corresponds to the exhaust port provided for the real space. The correction step includes correcting the analysis formula based on the difference detected in the difference detection step. The estimation step includes estimating the actual carbon dioxide concentration distribution using the analysis formula corrected in the correction step and the location information acquired in the location information acquisition step.

This aspect enables estimating, by correcting the analysis formula based on a difference in carbon dioxide concentration at a predetermined point in the indoor space (20) such as an exhaust port (first exhaust port 241), the carbon dioxide concentration distribution more accurately using a small number of sensors.

An estimation method according to a third aspect, which may be implemented in conjunction with the first aspect, further includes an actual value acquisition step, a difference detection step, and a correction step. The actual value acquisition step includes acquiring an actual value of carbon dioxide concentration at an exhaust port (first exhaust port 241) provided for the real space. The difference detection step includes detecting a difference between the actual value acquired in the actual value acquisition step and an analytic value of carbon dioxide concentration at an exhaust port (first exhaust port 241a) provided for the virtual space (20a) which corresponds to the exhaust port provided for the real space. The correction step includes correcting the analytic information based on the difference detected in the difference detection step.

This aspect enables estimating, by correcting the analytic information based on a difference in carbon dioxide concentration at a predetermined point in the indoor space (20) such as an exhaust port (first exhaust port 241), the carbon dioxide concentration distribution more accurately using a small number of sensors.

In an estimation method according to a fourth aspect, which may be implemented in conjunction with any one of the first to third aspects, the notification control step includes making notification by presenting, on a display device (81), information about the actual carbon dioxide concentration distribution estimated in the estimation step.

According to this aspect, information about the actual carbon dioxide concentration distribution estimated in the estimation step is presented on a display device (81), thus allowing the user to visually recognize information about the actual carbon dioxide concentration distribution.

In an estimation method according to a fifth aspect, which may be implemented in conjunction with any one of the first to fourth aspects, the estimation step includes approximating a shape of the carbon dioxide concentration distribution in a space surrounding the person (H1) present in the real space to be a predetermined stereoscopic shape.

This aspect enables simplifying the processing in the estimation step and thereby shortening the time it takes to have the estimation step done by approximating the shape of the carbon dioxide concentration distribution in a space surrounding the person (H1) present in the indoor space (20) to be a predetermined stereoscopic shape.

In an estimation method according to a sixth aspect, which may be implemented in conjunction with the fifth aspect, the estimation step includes estimating, when at least part of a first space (space A1) and at least part of a second space (space A2) overlap with each other, a carbon dioxide concentration distribution in a space (A3) where the first space and the second space overlap with each other by adding a carbon dioxide concentration in the second space to a carbon dioxide concentration in the first space. The first space is a space surrounding a first person (person H1) present in the real space. The second space is a space surrounding a second person (person H2) present in the real space.

According to this aspect, when a first space (space A1) and a second space (space A2) overlap with each other, a carbon dioxide concentration distribution in a space (A3) is estimated by adding the carbon dioxide concentration in the second space to the carbon dioxide concentration in the first space, thereby enabling estimating the carbon dioxide concentration distribution in the indoor space (20) more accurately.

In an estimation method according to a seventh aspect, which may be implemented in conjunction with the fifth or sixth aspect, the predetermined stereoscopic shape is a circular column having a bottom surface perpendicular to the height direction.

According to this aspect, the predetermined stereoscopic shape is a circular column having a bottom surface perpendicular to the height direction, thus enabling further simplifying the processing in the estimation step and thereby further shortening the time it takes to have the estimation step done.

Note that the features according to the second to seventh aspects are not essential features of the estimation method but may be omitted as appropriate.

A program according to an eighth aspect is designed to cause one or more processors to perform the estimation method according to any one of the first to seventh aspects.

This aspect enables accurately estimating, by using location information about a person (H1) who is present in an indoor space (20) and an analysis formula established based on simulations, a carbon dioxide concentration distribution in the indoor space (20) when the person (H1) is present in the indoor space (20).

An estimation system (1) according to a ninth aspect includes an analyzer (70), an extractor (71), an approximator (72), a location information acquirer (73), an estimator (74), and a notification controller (75). The analyzer (70) does simulations to derive, as analytic information, a carbon dioxide concentration distribution in a virtual space (20a). The simulations are done based on three-dimensional information about an indoor space (20), first environmental information about an environment in the indoor space (20), second environmental information about an outdoor environment, and virtual location information about a person's (H1) location that has been set in the virtual space (20a) corresponding to the indoor space (20). The extractor (71) extracts, from the analytic information, information about a virtual carbon dioxide concentration distribution at a point which has been arbitrarily set in a height direction in the virtual space (20a).

The approximator (72) establishes an analysis formula for approximating, based on the information about the virtual carbon dioxide concentration distribution extracted by the extractor (71), the carbon dioxide concentration distribution in the height direction. The location information acquirer (73) acquires location information about the person (H1) who is present in a real space within the indoor space (20). The estimator (74) estimates an actual carbon dioxide concentration distribution in the real space using the analysis formula established by the approximator (72) and the location information acquired by the location information acquirer (73). The notification controller (75) makes notification of information about the actual carbon dioxide concentration distribution estimated by the estimator (74).

This aspect enables accurately estimating, by using location information about a person (H1) who is present in an indoor space (20) and an analysis formula established based on simulations, a carbon dioxide concentration distribution in the indoor space (20) when the person (H1) is present in the indoor space (20).

REFERENCE SIGNS LIST

1 Estimation System
20 Indoor Space

20*a* Virtual Space
241 First Exhaust Port (Exhaust Port)
241*a* First Exhaust Port (Exhaust Port)
70 Analyzer
71 Extractor
72 Approximator
73 Location Information Acquirer
74 Estimator
75 Notification Controller
81 Display Device
A1 Space (First Space)
A2 Space (Second Space)
A3 Space (space where first and second spaces overlap
    with each other)
H1 Person (First Person)
H2 Person (Second Person)

The invention claimed is:

1. An estimation method executed by one or more processors coupled with at least one non-transitory memory, the method comprising:

an analysis step including doing simulations based on three-dimensional information about an indoor space, first environmental information about an environment in the indoor space, second environmental information about an outdoor environment, and virtual location information about a location of a person which has been set in a virtual space corresponding to the indoor space to derive, as analytic information, a carbon dioxide concentration distribution in the virtual space, the three-dimensional information, the first environmental information, the second environmental information and the virtual location information being stored in the at least one memory;

an extraction step including extracting, from the analytic information, information about a virtual carbon dioxide concentration distribution at a point which has been arbitrarily set in a height direction in the virtual space;

an approximation step including establishing an analysis formula for approximating the carbon dioxide concentration distribution in the height direction based on the information about the virtual carbon dioxide concentration distribution extracted in the extraction step;

a location information acquisition step including acquiring location information about the person who is present in a real space within the indoor space from a mobile device carried by the person present in the real space;

an estimation step including estimating an actual carbon dioxide concentration distribution in the real space using the analysis formula established in the approximation step and the location information acquired in the location information acquisition step; and a notification control step including making notification of information about the actual carbon dioxide concentration distribution estimated in the estimation step.

2. The estimation method of claim 1, further comprising:

an actual value acquisition step including acquiring, from a $CO_2$ sensor provided in proximity to an exhaust port, an actual value of carbon dioxide concentration at the exhaust port provided for the real space;

a difference detection step including detecting a difference between the actual value acquired in the actual value acquisition step and an analytic value of carbon dioxide concentration at an exhaust port provided in the virtual space which corresponds to the exhaust port provided for the real space; and a correction step including correcting the analysis formula based on the difference detected in the difference detection step, wherein the estimation step includes estimating the actual carbon dioxide concentration distribution using the analysis formula corrected in the correction step and the location information acquired in the location information acquisition step.

3. The estimation method of claim 1, further comprising:

an actual value acquisition step including acquiring, from a $CO_2$ sensor provided in proximity to an exhaust port, an actual value of carbon dioxide concentration at the exhaust port provided for the real space;

a difference detection step including detecting a difference between the actual value acquired in the actual value acquisition step and an analytic value of carbon dioxide concentration at an exhaust port provided in the virtual space which corresponds to the exhaust port provided for the real space; and a correction step including correcting the analytic information based on the difference detected in the difference detection step.

4. The estimation method of claim 1, wherein the notification control step includes making notification by presenting, on a display device, information about the actual carbon dioxide concentration distribution estimated in the estimation step.

5. The estimation method of claim 1, wherein the estimation step includes approximating a shape of the carbon dioxide concentration distribution in a space surrounding the person present in the real space to be a predetermined stereoscopic shape.

6. The estimation method of claim 5, wherein the estimation step includes estimating, when at least part of a first space surrounding a first person present in the real space and at least part of a second space surrounding a second person present in the real space overlap with each other, a carbon dioxide concentration distribution in a space where the first space and the second space overlap with each other by adding a carbon dioxide concentration in the second space to a carbon dioxide concentration in the first space.

7. The estimation method of claim 5, wherein the predetermined stereoscopic shape is a circular column having a bottom surface perpendicular to the height direction.

8. A non-transitory storage medium storing thereon a program designed to cause one or more processors coupled to at least one non-transitory memory to perform;

an analysis step including doing simulations based on three-dimensional information about an indoor space, first environmental information about an environment in the indoor space, second environmental information about an outdoor environment, and virtual location information about a location of a person which has been set in a virtual space corresponding to the indoor space to derive, as analytic information, a carbon dioxide concentration distribution in the virtual space, the three-dimensional information, the first environmental information, the second environmental information and the virtual location information being stored in the at least one memory;

an extraction step including extracting, from the analytic information, information about a virtual carbon dioxide concentration distribution at a point which has been arbitrarily set in a height direction in the virtual space;

an approximation step including establishing an analysis formula for approximating the carbon dioxide concentration distribution in the height direction based on the information about the virtual carbon dioxide concentration distribution extracted in the extraction step;

a location information acquisition step including acquiring location information about the person who is present in a real space within the indoor space from a mobile device carried by the person present in the real space;

an estimation step including estimating an actual carbon dioxide concentration distribution in the real space using the analysis formula established in the approximation step and the location information acquired in the location information acquisition step; and a notification control step including making notification of information about the actual carbon dioxide concentration distribution estimated in the estimation step.

9. An estimation system comprising:

at least one memory; and one or more processors coupled with the at least one memory, wherein the one or more processors are configured, by executing a program stored in a non-transitory storage medium, to:

do simulations based on three-dimensional information about an indoor space, first environmental information about an environment in the indoor space, second environmental information about an outdoor environ-ment, and virtual location information about a location of a person which has been set in a virtual space corresponding to the indoor space and thereby derive, as analytic information, a carbon dioxide concentration distribution in the virtual space, the three-dimensional information, the first environmental information, the second environmental information and the virtual location information being stored in the at least one memory;

extract, from the analytic information, information about a virtual carbon dioxide concentration distribution at a point which has been arbitrarily set in a height direction in the virtual space;

establish an analysis formula for approximating the carbon dioxide concentration distribution in the height direction based on the information about the virtual carbon dioxide concentration distribution;

acquire location information about the person who is present in a real space within the indoor space from a mobile device carried by the person present in the real space;

estimate an actual carbon dioxide concentration distribution in the real space using the established analysis formula and the acquired location information; and make notification of information about the estimated actual carbon dioxide concentration distribution.

\*    \*    \*    \*    \*